(12) United States Patent
Powers et al.

(10) Patent No.: US 6,780,602 B2
(45) Date of Patent: Aug. 24, 2004

(54) TAXONOMIC IDENTIFICATION OF PATHOGENIC MICROORGANISMS AND THEIR TOXIC PROTEINS

(75) Inventors: Linda S. Powers, Logan, UT (US); Walther R. Ellis, Jr., Logan, UT (US); Christopher R. Lloyd, North Logan, UT (US)

(73) Assignee: Microbiosystems, Limited Partnership, Cheyenne, WY (US)

( * ) Notice: Subject to any disclaimer, the term of this patent is extended or adjusted under 35 U.S.C. 154(b) by 0 days.

(21) Appl. No.: 09/999,159

(22) Filed: Nov. 1, 2001

(65) Prior Publication Data

US 2003/0124532 A1 Jul. 3, 2003

(51) Int. Cl.$^7$ ................. G01N 33/53; G01N 21/00; G01N 21/29; C11Q 1/00; C12Q 1/70
(52) U.S. Cl. .............. 435/7.1; 435/4; 435/5; 435/7.2; 422/82.05; 436/164; 436/172; 436/536; 436/538
(58) Field of Search ............. 435/5, 6, 7.2, 7.4, 435/7.32, 188, 283.1, 285.2, 286.1, 286.2, 286.5, 286.7, 287.2, 7.1, 7.8, 29, 34; 436/527, 528, 531, 535, 518, 523, 524, 526, 536, 538; 536/22.1, 23.1, 24.3, 24.31, 24.32, 24.33; 564/152, 50, 68.1; 422/82.05, 82.08, 169, 172

(56) References Cited

U.S. PATENT DOCUMENTS

| | | |
|---|---|---|
| 4,746,604 A | 5/1988 | Mowshowitz |
| 5,089,395 A | 2/1992 | Snyder et al. |
| 5,415,997 A | 5/1995 | Atrache et al. |
| 5,415,999 A | 5/1995 | Saul et al. |
| 5,648,227 A | 7/1997 | Basboll |
| 5,709,994 A | 1/1998 | Pease et al. |
| 5,731,148 A | 3/1998 | Becker et al. |
| 5,741,662 A | 4/1998 | Madsen et al. |
| 5,760,406 A * | 6/1998 | Powers ............... 250/461.2 |
| 5,763,158 A | 6/1998 | Bohannon |
| 5,821,066 A | 10/1998 | Pyle et al. |
| 5,888,760 A | 3/1999 | Godsey et al. |
| 5,912,115 A | 6/1999 | Hyman et al. |
| 5,948,624 A | 9/1999 | Rothschild et al. |
| 5,958,790 A | 9/1999 | Cerny |
| 5,965,456 A | 10/1999 | Malmqvist et al. |
| 5,968,766 A * | 10/1999 | Powers ..................... 435/29 |
| 5,972,715 A | 10/1999 | Celentano et al. |
| 5,976,827 A | 11/1999 | Jeffrey et al. |
| 6,001,556 A | 12/1999 | Charych et al. |
| 6,017,722 A | 1/2000 | Becvar et al. |
| 6,051,388 A | 4/2000 | Bodenhamer |
| 6,087,088 A | 7/2000 | Piran et al. |
| 6,124,102 A | 9/2000 | Fodor et al. |
| 6,159,689 A | 12/2000 | Parton |
| 6,184,012 B1 | 2/2001 | Neri et al. |
| 6,190,856 B1 | 2/2001 | Li |
| 6,190,878 B1 | 2/2001 | Pierson et al. |
| 6,197,568 B1 | 3/2001 | Marks et al. |
| 6,214,628 B1 | 4/2001 | Lakowicz et al. |
| 6,225,046 B1 | 5/2001 | Vesey et al. |
| 6,342,396 B1 * | 1/2002 | Perrin et al. ............. 436/518 |
| 2002/0187464 A1 * | 12/2002 | Klempner et al. ........... 435/5 |
| 2003/0060663 A1 * | 3/2003 | Griffin et al. ............. 564/152 |

FOREIGN PATENT DOCUMENTS

WO     WO 98/49557     * 11/1998

OTHER PUBLICATIONS

Cantor and Schimmel, Biophysical Chemistry, Part II, pp. 443–448, W. H. Freeman and Co., 1980.*
Tian et al., European Journal of Biochemistry, vol. 267, pp. 4486–4494 (2000).*

* cited by examiner

*Primary Examiner*—James Housel
*Assistant Examiner*—Zachariah Lucas
(74) *Attorney, Agent, or Firm*—K. S. Cornaby

(57) ABSTRACT

The present invention describes a method for the binding of pathogenic microorganisms and their toxic proteins with ligands that have been covalently tethered at some distance from the surface of a substrate: distances of at least fifteen Å are required for microorganism binding ligand tethers and at least six Å are required for protein binding ligand tethers. The ligands described herein include heme compounds, siderophores, polysaccharides, and peptides specific for toxic proteins, outer membrane proteins and conjugated lipids. Non-binding components of the solution to be analyzed are separated from the bound fraction and binding is confirmed by detection of the analyte via microscopy, fluorescence, epifluorescence, luminescence, phosphorescence, radioactivity, or optical absorbance. By patterning numerous ligands in an array on a substrate surface it is possible to taxonomically identify the microorganism by analysis of the binding pattern of the sample to the array.

41 Claims, 1 Drawing Sheet

TAXONOMIC IDENTIFICATION OF PATHOGENIC MICROORGANISMS AND THEIR TOXIC PROTEINS

BACKGROUND OF THE INVENTION

The present invention relates to a method for the taxonomic identification of pathogenic microorganisms and the detection of their proteinaceous toxins.

Pathogenic microorganisms, particularly pathogenic bacteria which either occur naturally or which have acquired virulence factors, are responsible for many diseases which plague mankind. Many of these bacteria have been proposed as biowarfare agents. In addition, there is also the risk and likelihood that nonpathogenic microbes could also be used as pathogens after genetic manipulation (e.g., *Escherichia coli* harboring the cholera toxin).

Typical pathogenic bacteria include those responsible for botulism, bubonic plague, cholera, diphtheria, dysentery, leprosy, meningitis, scarlet fever, syphilis and tuberculosis, to mention a few. During the last several decades, the public perception has been one of near indifference in industrialized nations, principally because of successes that have been achieved in combating these diseases using antibiotic therapy. However, bacteria are becoming alarmingly resistant to antibiotics. In addition, there have been recent revelations of new roles that bacteria perform in human diseases such as *Helicobacter pylori* as the causative agent of peptic ulcers, *Burkholderia cepacia* as a new pulmonary pathogen and *Chlamydia pneumoniae* as a possible trigger of coronary heart disease. Apart from those pathogens, various socioeconomic changes are similarly contributing to the worldwide rise in food-borne infections by bacteria such as *Escherichia coli*, Salmonella spp., Vibrio spp., and *Campylobacter jejuni*.

Potential infections are also important considerations in battlefield medicine. A number of bacterial pathogens, including *Bacillis anthracis* and *Yersinia pestis* and their exotoxins, have been used as weapons. And there is always the risk that nonpathogenic microbes can be engineered to be pathogenic and employed as biowarfare agents.

Pathogenic microorganisms are also of concern to the livestock and poultry industries as well as in wildlife management. For example, *Brucella abortus* causes the spontaneous abortion of calves in cattle. Water supplies contaminated with exotoxin-producing microorganisms have been implicated in the deaths of bird, fish and mammal populations. More recently, mad cow disease has been traced to the oral transmission of a proteinaceous particle not retained by filters. Thus, there is clearly a need for rapid and inexpensive techniques to conduct field assays for toxic proteins and pathogenic microorganisms that plague animals as well as humans.

As a general proposition, bacterial contamination can be detected by ordinary light microscopy. This technique, however, is only of limited taxonomic value. The investigation and quantitation of areas greater than microns in size are difficult and time consuming. Many commercially available systems rely on the growth of cultures of bacteria to obtain sufficiently large samples (outgrowth) for the subsequent application of differential metabolic tests for species (genus) identification. However, techniques requiring bacterial outgrowth may fail to detect viable but nonculturable cells. To the contrary, the growth media employed may favor the growth of bacteria with specific phenotypes.

More sensitive and more rapid typing schemes are described in "Strategies to Accelerate the Applicability of Gene Amplification Protocols for Pathogen Detection in Meat and Meat Products" by S. Pillai and S. C. Ricke (*Crit. Rev. Microbiol.* 21(4), 239–261 (1995)) and "Molecular Approaches for Environmental Monitoring of Microorganisms" by R. M. Atlas, G. Sayler, R. S. Burlage and A. K. Bej (*Biotechniques* 12(5), 706–717 (1992)). Those techniques employ the polymerase chain reaction (PCR) for amplification of bacterial DNA or RNA, followed by nucleic acid sequencing to detect the presence of a particular bacterial species. Such general amplification and sequencing techniques require technical expertise and are not easily adaptable outside of specialized laboratory conditions. PCR-based techniques utilize the inference of microbial presence since these techniques provide only a positive analysis whenever an intact target nucleic acid sequence, not necessarily a microbe, is detected. PCR is also unable to detect the presence of toxic microbial proteins. Moreover, the detection of specific microorganisms in environmental samples is made difficult by the presence of materials that interfere with the effectual amplification of target DNA in 'dirty' samples.

Mass spectral analysis of volatile cell components (e.g., fatty acids) after sample lysis or pyrolysis has been used for the detection of bacteria and viruses. One description of the methods used to detect microorganisms with this method can be found in "Characterization of Microorganisms and Biomarker Development from Global ESI-MS/MS Analyses of Cell Lysates" by F. Xiang, G. A. Anderson, T. D. Veenstra, M. S. Lipton and R. D. Smith (*Anal. Chem.* 72 (11), 2475–2481 (2000)). Unfortunately, identification of the analyte is unreliable as the compositions of a microbe's volatile components change depending upon different environmental growth conditions.

Another approach utilizes immunochemical capture as described in "The Use of Immunological Methods to Detect and Identify Bacteria in the Environment" by M. Schlotter, B. Assmus and A. Hartmann (*Biotech. Adv.* 13, 75–80 (1995)), followed by optical detection of the captured cells. The most popular immunoassay method, enzyme-linked immunosorbent assay (ELISA), has a detection limit of several hundred cells. This is well below the $ID_{50}$ of extremely infectious bacteria such as *Shigella flexneri*. Piezoelectric detection techniques, such as those described by "Development of a Piezoelectric Immunosensor for the Detection of *Salmonella typhimurium*" by E. Prusak-Sochaczewski and J. H. T. Luong (*Enzyme Microb. Technol.* 12: 173–177 (1990)) are even less sensitive having a detection limitation of about $5 \times 10^5$ cells. A recent report entitled "Biosensor Based on Force Microscope Technology" by D. R. Baselt, G. U. Lee and R. J. Colton (*Biosens. & Bioelectron.* 13, 731–739 (1998)) describes the use of an atomic force microscope (AFM) to detect immunocaptured cells; this method has little utility outside a laboratory setting and when the sample volumes are large. Immunoassays are also presently used in the trace analysis of peptides and proteins.

Moreover, the prior art has made extensive use of immobilized antibodies in peptide/protein/microorganism capture. Those techniques likewise involve significant problems because the antibodies employed are very sensitive to variations in pH, ionic strength and temperature. Antibodies are susceptible to degradation by a host of proteolytic enzymes in "dirty" samples. In addition, the density of antibody molecules supported on surfaces (e.g., microwell plates or magnetic beads) is not as high as is frequently necessary. A good summary of the state of the art, still up-to-date, is "Microbial Detection" by N. Hobson, I. Tothill and A. Turner (*Biosens. & Bioelectron.* 11, 455–477 (1996)).

Medical and military considerations call for better toxin and pathogen detection technologies. Real-time assessment of battlefield contamination by a remote sensing unit is necessary to permit and facilitate rapid diagnosis for administration of appropriate counter-measures. A microbe/toxic protein sensor useful in such situation requires the ability to globally discriminate between pathogens and non-pathogens. In addition, such techniques require high sensitivity when less than 100 cells are present and analysis that can be completed in the field in less than 15 minutes. Such techniques should be able to recognize pathogens and provide some assessment of strain virulence or toxigenicity.

To date, common approaches used for the identification of pathogenic microorganisms and their proteinaceous toxins have employed immunological methodologies. Immunological methods suffer from the sensitivity of antibodies toward pH, ionic strength, and temperature; the antibodies themselves are subject to proteolysis and require careful storage conditions. To overcome these problems the present invention describes the capture of microorganisms and their proteinaceous toxins using non-antibody based ligands. It is accordingly an object of the present invention to provide a method for taxonomically evaluating microbes and proteins that overcome the foregoing disadvantages of technologies that depend upon antibodies.

It is a more specific object of the invention to provide a method for taxonomically evaluating microbes and proteins that has the capability of discriminating between specific microbial species, pathogens and nonpathogens, and can be likewise used to identify microbial proteins of diagnostic utility.

SUMMARY OF THE INVENTION

The present invention demonstrates the ability of heme compounds, siderophores, polysaccharides and peptides to bind to pathogenic microorganisms and their proteinaceous toxins; taxonomic identification of a microorganism is attained thorough analysis of the number and kind of ligands to which it binds. The development of this method was done to overcome the aforementioned limitations of antibody-based technologies. The concept of the present invention resides in a method for the taxonomic identification of microorganisms in which microbes are captured through the binding of microbial receptors to specific ligands. A microorganism-containing sample is contacted by the ligand, with the ligand being either tethered to a surface or conjugated to a marker. The target microbe (bacteria, virus, fungi, protozoa, rickettsiae, or other cell) or proteinaceous material (toxin) is then separated from the non-binding sample components and unbound ligand as by washing, magnetic separation or chromatography. Finally, the sample is interrogated by an appropriate method to determine if the ligand has been bound to the target by detecting signals endogenous to the target or marker.

Electromagnetic radiation is one method used to detect the presence of metabolites characteristic of living microbes, e.g., reduced pyridine nucleotides or other fluorescent metabolites, other biomolecules, e.g., notably tryptophan or tyrosine in proteins, or incorporated dyes for the detection of the presence of the captured microorganisms and/or toxins in accordance with the practice of the invention. For example, if the ligand contains a fluorescent dye, the sample will fluoresce after washing, since the ligand is bound to the cells and the excess is washed away. Other markers, including luminescent, phosphorescent, radioactive and/or colorometric compounds, can be conjugated to the ligand and used to identify a microbe and/or proteinaceous toxin in a similar manner.

One specific method to detect capture of microorganisms or toxic proteins is described in U.S. Pat. Nos. 5,760,406 and 5,968,766, where electromagnetic radiation is directed, for example, onto the surface of a ligand-conjugated substrate that has been treated with an analyte-containing solution as outlined above. This detection method could be used to determine if binding of an analyte has occurred. Other detection methods, appropriate for the specific kind of marker conjugated to the ligand, can also be employed to determine if the ligand has been specifically bound to a microorganism or toxic protein. An example mentioned previously uses a fluorescent dye conjugated to a ligand coupled to detection of a microbe via fluorescence characteristic of the dye after (1) contact between the microbe and ligand and (2) washing away excess dye-conjugated ligand. It is important to note that if optical methods are used to detect the captured microbe or protein the tether should not be photocleavable, e.g., the tether should be photostable.

Thus, the method of the present invention does not depend on classical antigen-antibody recognition. On the contrary, the concepts of the present invention make use of relatively inexpensive reagents in the capture of microorganisms and microbial proteins contained in the sample.

In one embodiment of the invention, sensor chips (or beads) are employed. These chips should be formed from a suitable support material such as glass or plastic substrates (e.g., poly(propylene) or poly(vinyl acetate)) that will be compatible with both the chemistries used to conjugate the linker and ligand to the surface and the detection method employed. The sensor chip is formed of a patterned array defining a plurality of sections on the surface of the sensor chip, and each section has bonded thereto a different ligand capable of molecularly recognizing a specific microbial protein or microbial receptor, and hence the microbe itself. Microbial receptors would include, for example, proteins residing in the outer membrane of the microbial cell, pilus or flagellum, which is exposed to the aqueous environment surrounding the cell. The ligand for pathogen/protein capture bonded to the surface of the sensor chip can and should be varied. In general, such ligands may be characterized as heme compounds, siderophores, polysaccharides and anti-adhesion peptides capable of capturing a wide variety of microorganisms and toxic proteins. These ligands can thus be immobilized or bonded to the surface of the sensor chip through an appropriately sized cross-linker also having the capability of reacting with the ligands, whereby the coupling agent establishes a chemical tether between the surface of the sensor chip and the ligand capable of reaction with a variety of different microorganisms and proteins. The sensor chips and arrays (1) are exposed to a solution containing microorganisms or toxic proteins, (2) the non-binding constituents of the solution are removed, (3) followed by interrogation of the ligand-tethered surfaces to detect analyte binding. Analysis of the type or pattern of ligand-tethered surfaces found to have captured the microorganism(s), or microbial proteins not contained within intact microbial cells, can be used to taxonomically identify a microorganism or its toxic protein.

Thus, the present invention can be used rapidly to identify microorganisms without the need for growing a culture of the microorganism and then microscopically examining the culture thus produced. Likewise, low levels of toxic microbial proteins can similarly be identified. It is also unnecessary to employ enzymes or antibodies in the capture of microbial metabolites as is often used in the prior art. These, and other objects, features and advantages of the present invention will become apparent upon review of the follow-

DETAILED DESCRIPTION OF THE INVENTION

Figure 1:
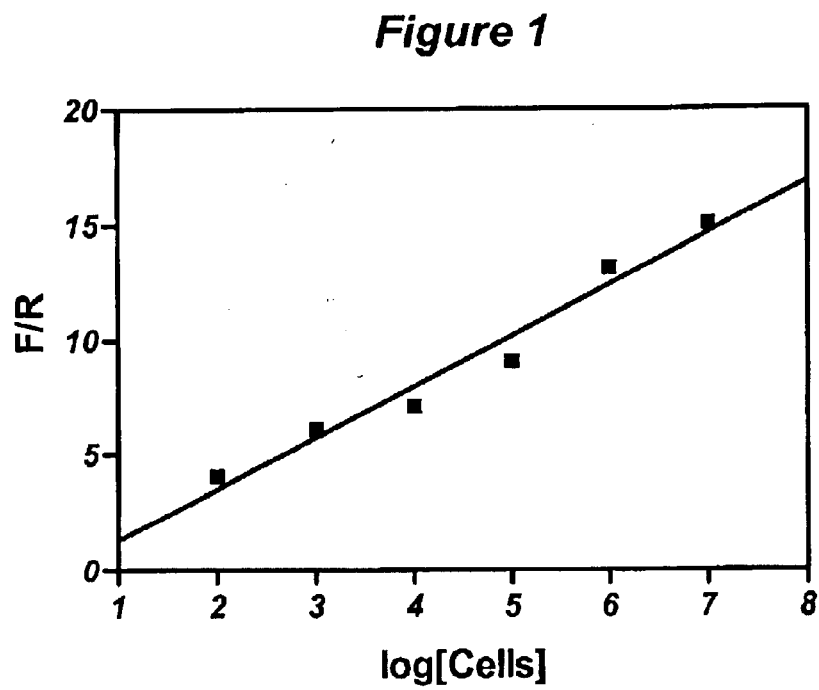
FIG. 1 shows the capture of *Salmonella typhimurium* on a glass microscope slide coated with tethered heme. Detection of this pathogenic bacterium was accomplished according to the method and apparatus outlined in U.S. Pat. No. 5,968,766 to Powers.

The capture of a pathogenic bacterium (*Salmonella typhimurium*) with tethered heme, as outlined in the present invention, is shown in FIG. 1. (The method and apparatus outlined in U.S. Pat. No. 5,968,766 was employed for the detection of the captured bacteria. Although numerous compatible bacterial detection methods could have been employed, this method was used due to its ability to detect such small numbers of bacteria on the slide.) Inspection of the figure shows that the detection limit (<100 cells) of the captured microorganism using a tethered heme ligand is lower than that observed using immunological methods (ca. 400 cells under optimal conditions). Binding between the microorganism and the heme ligand is not as sensitive to pH, ionic strength and temperature as is binding to an antibody. The heme ligand is also less expensive, requires less careful storage and is not susceptible to proteolysis as are antibodies.

Figure 2:
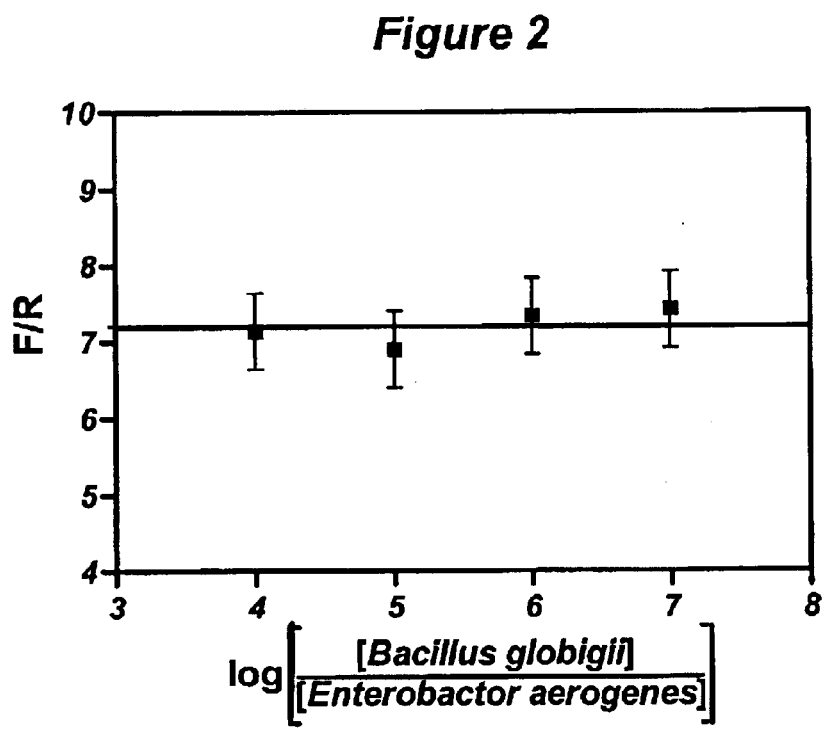
FIG. 2 shows the capture of *Enterobactor aerogenes* diluted in various concentrations of *Bacillus globigii* on a glass microscope slide coated with tethered heme. Detection of this pathogenic bacterium was accomplished according to the method and apparatus outlined in U.S. Pat. No. 5,968,766 to Powers.

FIG. 2 shows the tethered heme capture of a pathogenic bacterium (*Enterobactor aerogenes*) that has been diluted to the same concentration in solutions of a nonpathogen (*Bacillus globigii*). This figure shows that the tethered heme-coated slide is able to effectively capture the pathogenic bacteria from a solution even when the nonpathogen to pathogen ratio is $10^7:1$. Detection of the captured bacteria was accomplished with the apparatus outlined in U.S. Pat. No. 5, 968,766 to Powers.

In one embodiment of the present invention, a sample containing a biological analyte, such as an unknown analyte microorganism or protein toxin, is first contacted by the ligand. The ligand can be tethered to a surface of either a chip or bead. Binding efficiency is dependent upon the length of the tether. Microbes are found to bind most efficiency to ligands that are around 40 Å long. Ligands directed to microbes are covalently attached to the substrate surface by tethers that are at least 15 Å in length; ligands directed to proteinaceous toxins are at least six Å long. The analyte is then physically separated from the non-binding sample. Analytes captured by ligands tethered to a surface can be separated from non-binding components of the sample by simply washing the surface of the chip or bead. The surface of the substrate is then interrogated to determine if binding of the ligand has occurred. The detection of bound microbes on the substrate surface can be made with: microscopy, intrinsic fluorescence, conjugate dye fluorescence, radioactivity, luminescence, phosphorescence, and/or optical absorbance. Identification of the microbe or protein is determined by the identity of the ligand. It is important to note that the tether should not be photocleavable (e.g., the tether should be photostable), or otherwise chemically labile in the solution used to wash the ligand-tethered surface.

In one embodiment of the invention, a sample containing an unknown analyte microorganism or protein is first contacted with the sensor chip. The sensor chip is formed of a substrate, such as glass, having a series of sections on the surface thereof. Each section has a different ligand bonded thereto, so as to be capable of binding to specific analytes. The ligands are capable of binding to the analyte for capture, and the presence of the captured analyte is detected using a fluorescence detection system, for example, disclosed and claimed in U.S. Pat. Nos. 5,760,406 and 5,968,766 and via the intrinsic fluorescence of the proteinaceous toxins. Thus, the ligand of each of the sections of the sensor chip has the capability of capturing a specific microbial cell or microbial protein. The used chip can be saved and used to grow out the captured microorganisms as well.

In an alternate embodiment of the invention, a sample containing an unknown analyte (microorganism, proteinaceous toxin or other protein) is first contacted with a ligand conjugated to a marker, including, but not limited to, a fluorescent dye. The non-binding sample components and excess ligand are separated from the ligand-bound analyte; this separation can be accomplished by centrifugation (for cells), magnetic sedimentation or chromatography (for proteins). The detection of binding between the analyte and ligand, and thus taxonomic identification of the analyte, is accomplished by detection of the marker (e.g., fluorescence of the dye-conjugate in the example above).

In another embodiment of the invention, a sample containing an unknown analyte (microorganism or protein) is first contacted with a ligand tethered to a substrate surface with a linker of appropriate length, as noted above. Physical separation and washing remove non-binding components of the solution. As will be appreciated by those skilled in the art, the captured microorganism or protein can be treated with a reactive marker, provided the marker does not react with either the substrate surface or the ligands. Detection of the marker on the area of the surface associated with the ligand(s) that have been exposed to the analyte indicates the presence of a specific analyte.

In a preferred embodiment of the invention, the ligands used in the present invention may be taken from the group comprised of heme compounds, siderophores, polysaccharides (including oligosaccharides) and peptides.

As is also well known to those skilled in the art, animal pathogens generally possess heme uptake capability, and thus heme compounds can be used to capture a number of pathogenic species. In addition to heme compounds, other ligands in the form of high-affinity iron chelators, generally referred to as siderophores, can also be used to capture many strains of pathogenic bacteria. Included among such siderophores are alcaligin, mycobactins, pyochelin, staphyloferrin, vibriobactins and yersiniabactins.

As is also well known to those skilled in the art and as mentioned above, discrimination of animal pathogens by binding to heme compounds and siderophores that have been labeled with markers is also possible. An example would include the incubation of bacteria-containing solutions with a siderophore or heme compound that has been conjugated with a fluorescent, luminescent, phosphorescent, chemiluminescent, or radioactive compound. After washing the cells, detection of animal pathogens can be made by standard fluorescence, colorimetric or radiation detection-techniques. The binding of animal pathogens to heme compounds and siderophores that are tethered to a support can also be exploited to separate these microbes from environmental samples, e.g., water, for the purpose of concentration and/or purification.

cal synthesis or isolation from spent microbial culture media. Oligosaccharide ligands can be produced by chemical synthesis or isolated from eukaryotic tissue. Heme compounds can be produced typically by chemical synthesis using protoporphyrin IX as a starting reagent.

TABLE I

Bacterial Characteristics for Siderophore, Oligosaccharide and Hemin Binding

| Bacterial Species | Disease Caused | Siderophore Binding? | Oligosaccharide Binding? | Hemin Binding? | Exotoxin Produced? |
|---|---|---|---|---|---|
| Bacillus anthracis | Anthrax | unknown | a pulmonary oligosaccharide | unknown | anthrax toxin |
| Bordetella pertusis | Whooping cough | Alcaligin, others | N-acetyl-glucosamine | Yes | pertussis toxin |
| Clostridium botulinum | Botulism | unknown | unknown | Yes | botulinum toxin A |
| Clostridium perfringens | Gas gangrene | unknown | unknown | unknown | α-toxin |
| Clostridium tetani | Tetnus | unknown | unknown | unknown | tetanus toxin |
| Corynebacterium diphthariae | Diphtheria | Aerobactin | unknown | unknown | diphtheria toxin |
| Escherichia coli 0157:H7 | Numerous infections | many | Globobiose, others | Yes | Shiga-like toxin, others |
| Haemophilus influenzae | Meningitis | Enterobactin | GalNAcβ(1–4)Gal, others | Yes | unknown |
| Helicobacter pylori | Gastric ulcers | unknown | a mucosal oligosaccharide | unknown | vacuolating cytotoxin A |
| Klebsiella pneumoniae | Numerous infections | many | GalNAcβ(1–4)Gal, others | Yes | unknown |
| Mycobacterium tuberculosis | Tuberculosis | Mycobactin T | unknown | unknown | unknown |
| Neisseria meningitidis | Meningitis | many | unknown | Yes | unknown |
| Pseudomonas aeruginosa | Numerous infections | Pyochelin, others | Asialo $G_{M1}$, others | Yes | exotoxin A, elastase, others |
| Salmonella typhi | typhoid fever | many | unknown | Yes | Yes |
| Serratia marescens | numerous infections | Aerobactin, Ferrioxamine B | Yes | Yes | serralysin |
| Shigella dysenteriae | dysentery | Enterobactin, Aerobactin | Yes | Yes | Shiga toxin |
| Staphylococcus aureus | numerous infections | Staphyloferrin, others | GalNAcβ(1–4)Gal | Yes | several superantigens |
| Streptococcus pneumoniae | pneumonia, meningitis | unknown | GlcNAcetyl(1–3)Gal, others | Yes | streptolysin O |
| Vibrio cholerae | cholera | Vibriobactin, others | Yes | Yes | cholera toxin |
| Yersinia pestis | bubonic plague | Yersiniabactin, others | unknown | Yes | YopE, others |

In addition to heme compounds and siderophores, eukaryotic surface epitopes (peptides or carbohydrates), which are recognized by microbial cell receptors, can likewise be used as ligands in the practice of the present invention. These ligands include naturally occurring oligosaccharides and polysaccharides as well as those available by chemical synthesis. Other oligosaccharides and their affinity to pathogens from various microorganisms are described by K. A. Karlsson "Microbial Recognition of Target Cell Glycoconjugates" (*Structural Biology* 5:622–635 (1995)).

The characteristics of a number of pathogenic bacterial organisms, including the disease caused by each species and their binding characteristics with siderophores, oligosaccharides and heme compounds are set forth in Table I. These characteristics can be used in the capture and identification of such species.

Peptide ligands can typically be identified by affinity panning of libraries of oligopeptides and then synthesized chemically. Siderophore ligands can be produced by chemi- Toxins that contain at least one tryptophan or a few tyrosines per molecule can be detected by tryptophan/tyrosine fluorescence after capture using a tethered peptide. A variety of microbes, including algae, fungi, and bacteria, export exotoxins that are amenable to detection using this technology.

Table II contains examples of toxic, bacterial proteins that can be (1) captured using the technology described herein, and (2) ultimately detected via means of their intrinsic fluoresence. It is important to note that, for *Staphylococcus aureus* enterotoxin B, which represents the most unfavorable case in Table II (due to the presence of just one Trp and 22 Tyr), the following fluorescence study of the sole Trp residue has appeared: B. R. Singh, M. L. Evenson and M. S. Bergdahl "Structural Analysis of Staphylococcal Enterotoxins B and C1 Using Circular Dichroism and Fluorescence Spectroscopy" (*Biochemistry* 27: 8735–8741 (1988)). As is well known to those skilled in the art, detection of tryptophan/tyrosine fluorescence (normalized to the scattered excitation signal) is sufficient to indicate that spores, nonviable cells, viable vegetative bacterial or fungal cells, viruses, or a microbial toxin are present (i.e., bound to a ligand) on the surface of a sector of the sensor chip.

TABLE II

Amino acid Counts for Selected Bacterial Toxins

| Bacterium | Toxin | No. Amino Acids | No. Trp | No. Tyr |
|---|---|---|---|---|
| B. anthracis | protective antigen | 753 | 7 | 27 |
| B. anthracis | lethal factor | 770 | 5 | 35 |
| B. cereus | phospholipase C | 245 | 9 | 15 |
| B. pertussis | pertussis toxin | 952 | 11 | 50 |
| C. botulinum | toxin A | 1296 | 15 | 67 |
| C. difficile | toxin A | 2366 | 25 | 166 |
| C. perfringens | iota-toxin | 346 | 4 | 18 |
| C. tetani | tetanus toxin | 1421 | 13 | 78 |
| C. diphtheriae | diphtheria toxin | 534 | 5 | 16 |
| E. coli | alpha-hemolysin | 1023 | 3 | 38 |
| H. pylori | vacuolating cytotoxin A | 808 | 8 | 14 |
| L. monocytogenes | listeriolysin O | 523 | 7 | 23 |
| P. aeruginosa | elastase | 301 | 4 | 22 |
| S. marescens | serralysin | 470 | 7 | 19 |
| S. dysenteriae | Shiga toxin | 638 | 7 | 17 |
| S. aureus | enterotoxin B | 239 | 1 | 22 |
| S. aureus | toxic-showk toxin-1 | 194 | 3 | 9 |

Thus, as described above, a different ligand is tethered to each of the sections of the sensor chip. The sensor chip is then contacted with a sample containing unknown organisms or proteins, whereby specific ligands on the surface of the chip bind to specific analytes, selectively capturing them. The unbound analytes are then washed away with an appropriate solution (such as a phosphate-buffered saline); and the sensor chip is then subjected to an appropriate detection technique. One possible technique used to detect the presence of bacteria on the sections of the sensor chip is disclosed in U.S. Pat. Nos. 5,760,406 and 5,968,766, wherein the described apparatus utilizes electromagnetic radiation of appropriate wavelengths to excite fluorescence characteristic of the presence of bound analytes.

As is well known to those skilled in the art, if a tethered ligand used to capture an analyte is itself fluorescent then this fluorescence may change upon binding to the analyte. (This change in fluorescence could be manifest as either a change in intensity or a shift of the characteristic fluorescence energy.) This change in the fluorescence of the tethered ligand can be used to confirm detection of the analyte.

In the presence of the present invention, a sample containing unknown microbes can be contacted with the sensor chip, whereby one or more receptors of the bacteria react with various different ligands tethered to the various sections of the chip. Then, the fluorescence of the chip can be measured with a probe for the purpose of detecting which of the sections of the sensor chip have analytes bonded thereto. As examples, mycobacterial siderophores can be used to capture mycobacteria such as *Mycobacterium tuberculosis*. *Helicobacter pylori* can be captured using tethered N-acetylneuroaminyl-alpha-2,3-galactose. The peptide:

GADRSYLSFIHLYPELAGAGGGC can be tethered, by means of the terminal cysteine group to expressly capture free *Staphylococcus aureus* toxic-shock toxin-1. The peptide:

GHHKHHHGGGC can be tethered also by means of the terminal cysteine group, to specifically capture the surface-exposed protein A of *Staphylococcus aureus*, and hence this organism itself. The *Staphylococcus aureus* toxic-shock syndrome toxin-1-binding peptide was described by A. Sato, et al. in "Identification from a Phage Display Library of Peptides that Bind to Toxic Shock Syndrome Toxin-1 and that Inhibit Its Binding to Major Histocompatibility Complex (MHC) Class II Molecules" (*Biochemistry* 35, 10441–10447 (1996)).

As indicated above, determining the presence of a single captured microorganism or discrete microbial protein can identify some of the analytes of interest. In other cases, however, a series of two or more captured analytes of interest is indicative of the identity of a particular analyte. As an example, consider a sensor chip having an area of three sections along the horizontal axis and three sections along the vertical axis as illustrated below:

| | | |
|---|---|---|
| A1 | A2 | A3 |
| B1 | B2 | B3 |
| C1 | C2 | C3 |

In this example, the sections identified can be provided with the following ligands tethered to a specific section as set forth in the following table:

| Section Location | 3 x 3 Array Ligand |
|---|---|
| A1 | asialo $G_{M1}$ |
| A2 | hemin |
| A3 | pyochelin |
| B1 | GalNAcβGal |
| B2 | alcaligin |
| B3 | fibronectin (peptide fragment) |
| C1 | anti-*S. aureus* protein A peptide |
| C2 | staphyloferrin |
| C3 | ferrioxamine B |

It has been found that *Pseudomonas aeruginosa* can be identified as the microorganism when analytes are detected in sections A1, A2, A3, B1 and C3. Similarly, *Staphylococcus aureus* can be identified when sections A2, B1, B3, C1, C2 and C3 contain analyte captured thereon. In this case, capture of an analyte in section C1 is sufficient for taxonomic identification. Capture of cells in sections A2, B1, B3, C2 and C3 reinforces the result. The incorporation of multiple ligands targeting a given analyte onto a sensor chip, in effect, permits multiple, independent analyses to be carried out using a single sample. This increases the statistical reliability of the analytical outcome.

The various ligands are preferably tethered to a substrate by means of organic coupling agents which are themselves well known to those skilled in the art. When using a glass substrate, or a plastic whose surface that has been chemically oxidized to produce exposed hydroxyl groups, for the sensor chip, it is frequently preferred to employ, in the practice of the invention, organosilane compounds have the following general structure:

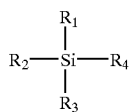

wherein $R_1$ through $R_4$ are each selected from the group consisting of hydrogen, alkyl groups containing 1 to 6 carbon atoms, aryl groups containing 6–12 carbons and alkoxy groups containing 1 to 4 carbon atoms, with at least one of $R_1$, $R_2$ and $R_3$ being an alkoxy group. $R_4$ is an organic group containing at least three carbon atoms and also containing a long linker bearing a functional group capable of reaction with the ligand. Without limiting the invention, suitable organic groups comprising the linker include polyamines, polyethers and poly(glycine). Also suitable for use in the practice of the invention are coupling agents containing other functional groups such as epoxy groups, amino groups and unsaturated functional groups, hydroxyl groups, thiol groups and the like, which are capable of reaction with the various ligands. Without limiting the invention as to theory, it is believed that the ligand reacts with the functional group, preferably a terminal functional group on the organosilane compound while the readily hydrolyzable alkoxy group attached directly to the silicon atom has the capability of reacting directly with the surface of the glass or plastic substrate of the sensor chips. This coupling agent (extended silane) may be alternatively constructed in situ by first reacting the parent silane with the surface of the sensor chip, followed by the chemical reactions needed to attach the linker to the immobilized silane. The ligand is then tethered to the surface of the glass or plastic through the coupling agent (i.e., silane bearing the organic linker). Further, the linker should be of sufficient length to present the ligand at the optimal distance (40 Ångstroms) from the surface of the chip. This observation is based on our determination that shorter distances results in decreased bacterial cell capture efficiency.

Thus the ligand tethered to the glass surface may be illustrated by the following:

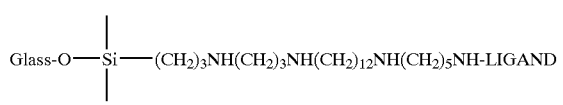

The ligand tethered to an oxidized plastic surface may be illustrated as above by replacing the "Glass-O—Si" moiety with C (carbon from the plastic polymer). The chemical reactions used in tethering ligands to the surface of the sensor chip are known to those skilled in the art and are described in the literature. Such reactions may be found in G. T. Hermanson *Bioconjugate Techniques* (San Diego: Academic Press, 1966); Hansson et al., "Carbohydrate-Specific Adhesion of Bacteria to Thin Layer Chromatograms: A Rationalized Approach to the Study of Host Cell Glycolipid Receptors" (*Analytical Biochemistry* 146: 158–163 (1985)); and, Nilsson et al., "A Carbohydrate Biosensor Surface for the Detection of Uropathogenic Bacteria" (*Bio/Technology* 12: 1376–1378 (December 1994)).

Illustrative of such reactions are those used to tether ferroxamine as a ligand to the surface of a glass sensor chip. In the first stage, a glass surface containing free hydroxyl groups is first reacted with a 2% solution of gamma-N-(aminopropyl)-gamma-aminopropyltrimethoxysilane to attach the silane to the glass surface:

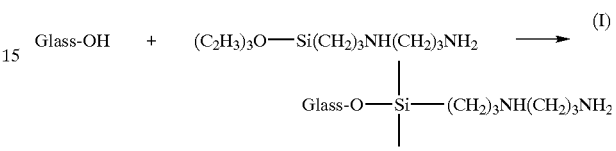

(I)

The product of that reaction can then be reacted with glutaraldehyde at a pH of about 8 to form the corresponding aldehyde:

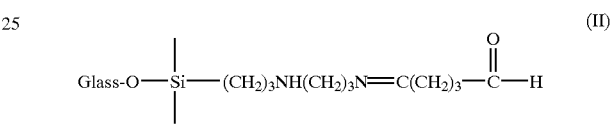

(II)

The aldehyde, in turn, can be reacted with a diamine (III) to yield IV:

$$H_2N(CH_2)_{12}NH_2 \quad (III)$$

(IV)

Next, the product of the preceding reaction is reacted with glutaraldehyde to introduce a (terminal) aldehyde group:

(V)

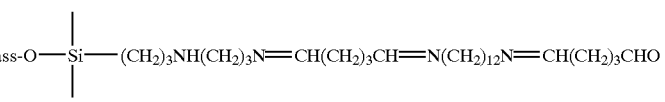

which can then be reduced using $NaCNBH_3$ to yield:

(VI)

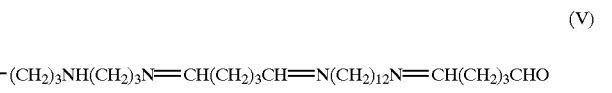

The foregoing silane coupling agent bonded to the surface can then be derivatized by reaction with deferrioxamine B (or DFA) at an alkaline pH to yield:

(VII)

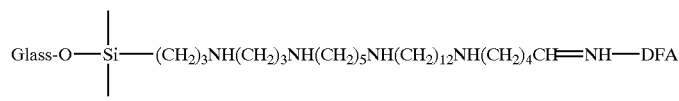

The DFA can then be complexed with Fe by reaction with a ferrous salt in aqueous medium to form the ligand.

It will be understood that various changes and modifications can be made in the determination, procedure, and formulation without departing from the spirit of the invention, especially as defined in the following claims:

What is claimed:

1. A method for taxonomic identification of a biological analyte comprising:
    (a) exposing a solution containing the analyte to a ligand specific for the analyte of interest that has been covalently tethered to a substrate surface with a photostable linker at a distance of about 40 Å for the capture of microorganisms;
    (b) separating the bound analyte from the non-binding components of the solution containing the analyte by physical separation, washing or both; and
    (c) interrogation of the ligand-tethered substrate surface for analyte binding.

2. The method of claim 1, wherein the biological analyte is selected from the group comprised of:
    (a) bacteria;
    (b) viruses;
    (c) rickettsiae;
    (d) protozoa; and
    (e) fungi.

3. The method of claim 1, wherein the ligand is a heme compound.

4. The method of claim 1, wherein the ligand is a siderophore.

5. The method of claim 1, wherein the ligand is a polysaccharide.

6. The method of claim 1, wherein the ligand is a peptide specific for an outer membrane protein.

7. The method of claim 1, wherein the ligand is a peptide specific for a conjugated lipid.

8. The method of claim 1, wherein the detection of the captured analyte is accomplished through microscopy.

9. The method of claim 1, wherein the detection of the captured biological analyte is accomplished through the intrinsic fluorescence arising from the fluorescence of naturally-occurring components.

10. The method of claim 1, wherein the detection of the captured analyte is accomplished through the fluorescence of a reactive dye conjugate exposed to the sample before capture of the analyte by the tethered ligand surface.

11. The method of claim 1, wherein the detection of the captured analyte is accomplished through the fluorescence of a reactive dye conjugate exposed to the sample after capture of the analyte by the tethered ligand surface.

12. The method of claim 1, wherein the detection of the captured analyte is accomplished through the radioactivity of a reactive compound exposed to the sample before capture of the analyte by the tethered ligand surface.

13. The method of claim 1, wherein the detection of the captured analyte is accomplished through the radioactivity of a reactive compound exposed to the sample after capture by the tethered ligand surface.

14. The method of claim 1, wherein the detection of the captured analyte is accomplished through the luminescence of a reactive dye conjugate exposed to the sample before capture of the analyte by the tethered ligand surface.

15. The method of claim 1, wherein the detection of the captured analyte is accomplished through the luminescence of a reactive dye conjugate exposed to the sample after capture of the analyte by the tethered ligand surface.

16. The method of claim 1, wherein the detection of the captured analyte is accomplished through the phosphorescence of a reactive dye conjugate exposed to the sample before capture of the analyte by the tethered ligand surface.

17. The method of claim 1, wherein the detection of the captured analyte is accomplished through the phosphorescence of a reactive dye conjugate exposed to the sample after capture of the analyte by the tethered ligand surface.

18. The method of claim 1, wherein the detection of the captured analyte is accomplished through the optical absorbance of a reactive dye conjugate exposed to the sample before capture of the analyte by the tethered ligand surface.

19. The method of claim 1, wherein the detection of the captured analyte is accomplished through the optical absorbance of a reactive dye conjugate exposed to the sample after capture of the analyte by the tethered ligand surface.

20. The method of claim 1, wherein the detection of the captured analyte is accomplished through the fluorescent quenching of the fluorescent tethered ligand surface upon binding of the analyte.

21. A method for taxonomic identification of a biological analyte comprising:
    (a) exposing a solution containing the analyte to an array of different ligands that have been covalently tethered to a substrate surface at about 40 Å;
    (b) separating the bound analyte on the ligand array from the non-binding components of the solution by physical separation, washing or both; and
    (c) interrogation of the ligand-tethered substrate surface for analyte binding.

22. The method of claim 21, wherein the ligands utilized in the array are tethered with a photostable linker at a distance of 40 Å from the substrate surface for the capture of microorganisms.

23. The method of claim 21, wherein the biological analyte is selected from the group comprising:
    (a) bacteria;
    (b) viruses;
    (c) proteinaceous toxin;
    (d) rickettsiae;
    (e) protozoa;
    (f) fungi; and
    (g) cytosolic protein.

24. The method of claim 21, wherein a ligand is a heme compound.

25. The method of claim 21, wherein one or more of the ligands is a siderophore.

26. The method of claim 21, wherein one or more of the ligands is a polysaccharide.

27. The method of claim 21, wherein one or more of the ligands is a peptide specific for an outer membrane protein.

28. The method of claim 21, wherein one or more of the ligands is a peptide specific for a conjugated lipid.

29. The method of claim 21, wherein the detection of a captured microorganism is accomplished through microscopy.

30. The method of claim 21, wherein the detection of the captured analyte is accomplished through the intrinsic fluorescence of the target.

31. The method of claim 21, wherein the detection of the captured analyte is accomplished through the fluorescence of a reactive dye conjugate exposed to the sample before capture of the analyte by the tethered ligand surface.

32. The method of claim 21, wherein the detection of the captured analyte is accomplished through the fluorescence of a reactive dye conjugate exposed to the sample after capture of the analyte by the tethered ligand surface.

33. The method of claim 21, wherein the detection of the captured analyte is accomplished through the radioactivity of a reactive compound exposed to the sample before capture of the analyte by the tethered ligand surface.

34. The method of claim 21, wherein the detection of the captured analyte is accomplished through the radioactivity of a reactive compound exposed to the sample after capture by the tethered ligand surface.

35. The method of claim 21, wherein the detection of the captured analyte is accomplished through the luminescence of a reactive dye conjugate exposed to the sample before capture of the analyte by the tethered ligand surface.

36. The method of claim 21, wherein the detection of the captured analyte is accomplished through the luminescence of a reactive dye conjugate exposed to the sample after capture of the analyte by the tethered ligand surface.

37. The method of claim 21, wherein the detection of the captured analyte is accomplished through the phosphorescence of a reactive dye conjugate exposed to the sample before capture of the analyte by the tethered ligand surface.

38. The method of claim 21, wherein the detection of the captured analyte is accomplished through the phosphorescence of a reactive dye conjugate exposed to the sample after capture of the analyte by the tethered ligand surface.

39. The method of claim 21, wherein the detection of the captured analyte is accomplished through the optical absorbance of a reactive dye conjugate exposed to the sample before capture of the analyte by the tethered ligand surface.

40. The method of claim 21, wherein the detection of the captured analyte is accomplished through the optical absorbance of a reactive dye conjugate exposed to the sample after capture of the analyte by the tethered ligand surface.

41. The method of claim 21, wherein the detection of the captured analyte is accomplished through the fluorescent quenching of the fluorescent tethered ligand surface upon binding of the analyte.

* * * * *